(12) United States Patent
Chen

(10) Patent No.: US 9,062,874 B2
(45) Date of Patent: Jun. 23, 2015

(54) ELECTRONIC CENSER

(71) Applicant: HON HAI PRECISION INDUSTRY CO., LTD., New Taipei (TW)

(72) Inventor: Po-Chou Chen, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 68 days.

(21) Appl. No.: 13/962,187

(22) Filed: Aug. 8, 2013

(65) Prior Publication Data

US 2014/0169028 A1 Jun. 19, 2014

(30) Foreign Application Priority Data

Dec. 19, 2012 (TW) .............................. 101148289 A

(51) Int. Cl.
*F21V 33/00* (2006.01)
*F21S 6/00* (2006.01)
*F21V 23/04* (2006.01)
*F21Y 101/02* (2006.01)

(52) U.S. Cl.
CPC ......... *F21V 33/0028* (2013.01); *F21V 33/0004* (2013.01); *F21S 6/001* (2013.01); *F21V 23/0471* (2013.01); *F21Y 2101/02* (2013.01)

(58) Field of Classification Search
CPC .................... F21Y 2113/002; F21Y 2113/005;
F21V 33/0004; F21V 33/00; F21V 19/006;
F21V 29/506; F21V 33/0028; F21V 23/06;
B05B 7/1686; F21S 10/04; F21S 8/035;
F21S 9/02; F24F 6/12
USPC ................... 362/96, 101, 643, 253, 551, 555;
422/123, 125; 392/386, 390, 392
See application file for complete search history.

(56) References Cited

U.S. PATENT DOCUMENTS

| 3,948,445 | A | * | 4/1976 | Andeweg | 239/53 |
| 5,647,052 | A | * | 7/1997 | Patel et al. | 392/390 |
| 5,651,942 | A | * | 7/1997 | Christensen | 422/125 |
| 7,093,949 | B2 | * | 8/2006 | Hart et al. | 362/96 |
| 7,604,378 | B2 | * | 10/2009 | Wolf et al. | 362/253 |
| 7,687,744 | B2 | * | 3/2010 | Walter et al. | 219/505 |
| 8,262,277 | B2 | * | 9/2012 | Hsiao | 362/643 |
| 8,529,078 | B2 | * | 9/2013 | Lee | 362/96 |
| 2008/0130266 | A1 | * | 6/2008 | DeWitt et al. | 362/96 |
| 2008/0223953 | A1 | * | 9/2008 | Tomono et al. | 239/102.2 |

* cited by examiner

*Primary Examiner* — Hargobind S Sawhney
(74) *Attorney, Agent, or Firm* — Novak Druce Connolly Bove + Quigg LLP

(57) ABSTRACT

An exemplary electronic censer includes a censer body, working fluid contained in the censer body, an incense branch, a fog generator, and a guiding tube. The incense includes a light guiding tube, a light source mounted on the light guiding tube, and a fog guiding tube surrounding the light guiding tube and spaced from the light guiding tube to define a chamber between the fog guiding tube and the light guiding tube. The fog generator is received in the censer body and converts the working fluid to fog. The guiding tube guides the fog from the censer body to the chamber to exhaust.

18 Claims, 1 Drawing Sheet

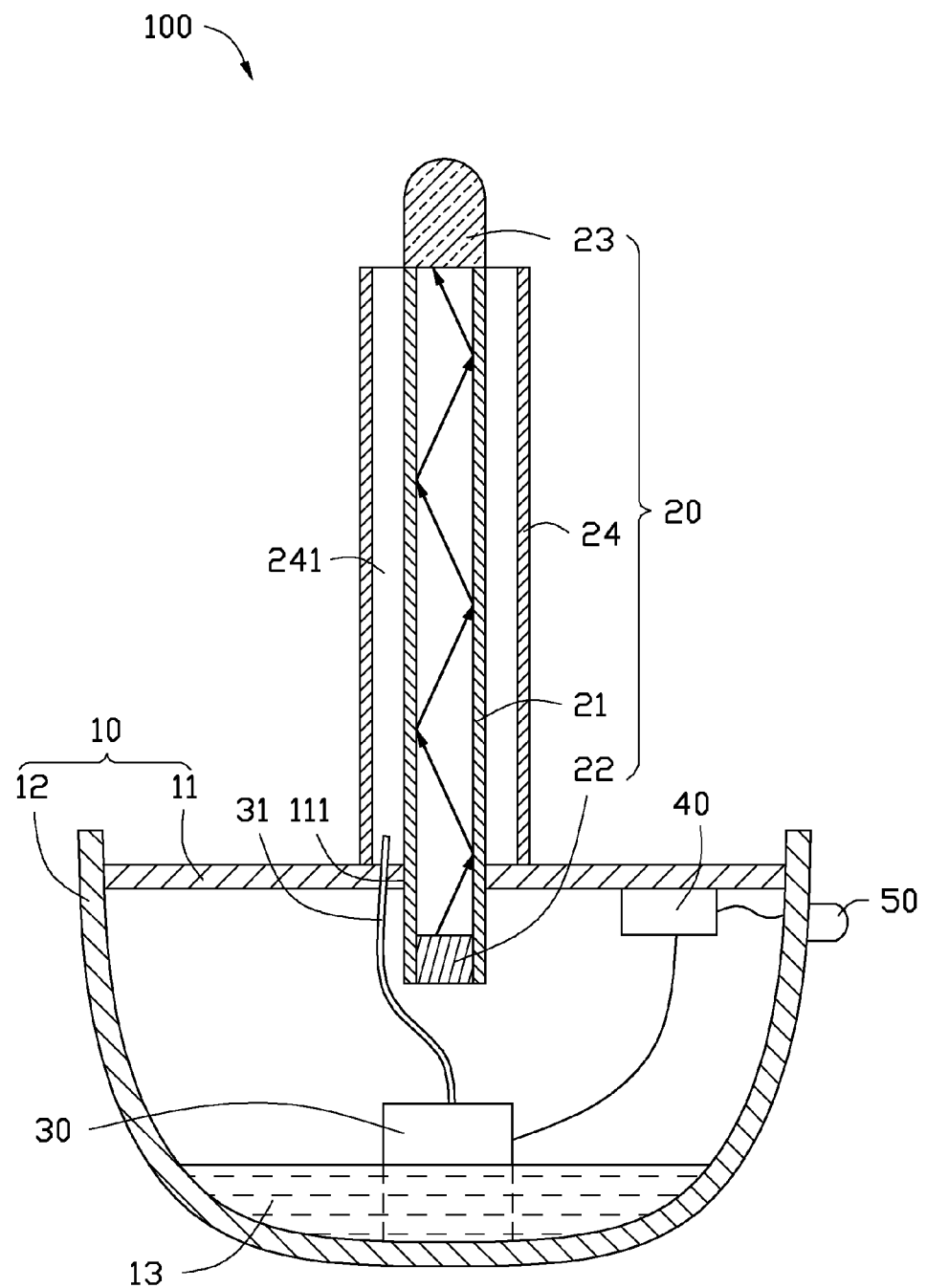

ELECTRONIC CENSER

BACKGROUND

1. Technical Field

The present disclosure generally relates to a censer, and particularly to an electronic censer.

2. Description of Related Art

Traditional censers are used for accommodating incenses, each of which mainly includes a rod made of bamboo and aromatic biotic materials coated on the rod. When the aromatic biotic materials are burned, they release large amounts of smoke. The burning incenses could ignite other articles to burn which may cause fire; furthermore, the released smoke not only pollutes the environment, but also is harmful to health.

Therefore, what is needed is to provide an electronic censer capable of overcoming the above shortcomings.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, like reference numerals designate corresponding parts throughout the several views.

The FIGURE is a cross sectional view of an electronic censer according to an exemplary embodiment of the present disclosure.

DETAILED DESCRIPTION

Embodiments of an electronic censer will now be described in detail below and with reference to the drawings.

Referring to the FIGURE, an electronic censer 100 includes a censer body 10, an incense branch 20 mounted on the censer body 10, a fog generator 30 received in the censer body 10, a controller 40 and a sensor 50 mounted on the censer body 10.

The censer body 10 is a hollow container and includes a bottom cover 12 and a top cover 11 engaging with the bottom cover 12. An opening 111 is defined at a central of the top cover 11. Working fluid 13 is received in the censer body 10.

The incense branch 20 is elongated and a bottom end thereof extends through the opening 111 and mounted on the top cover 11. The incense branch 20 includes a light guiding tube 21, a light source 22, a head member 23, and a fog guiding tube 24. The light guiding tube 21 is a cylindrical, transparent tube. A bottom portion of the light guiding tube 21 is received in the censer body 10. A top portion of the light guiding tube 21 is beyond the top cover 11. The light source 22 is received in a bottom end of the light guiding tube 21 and located in the censer body 10. The head member 23 is mounted on a top end of the light guiding tube 21 and covers the top end of the light guiding tube 21. In this embodiment, the head member 23 is made of glass or plastic. Preferably, a plurality of red powder is doped in the head member 23.

The fog guiding tube 24 is a cylindrical, opaque tube and surrounds the top portion of the light guiding tube 21. A bottom end of the fog guiding tube 24 is mounted on the top cover 11. A top end of the fog guiding tube 24 is coplanar with a bottom end of the head member 23. The fog guiding tube 24 is spaced from an outer surface of the top portion of the light guiding tube 21 to define a chamber 241 between the fog guiding tube 24 and the light guiding tube 21. A bottom end of the chamber 241 is closed by the top cover 11. A top end of the chamber 241 is opened.

Light emitted from the light source 22 is totally reflected by the fog guiding tube 24 and guided by the light guiding tube 21 to the head member 23, and travels through the head member 23 to illuminate. In this embodiment, the light source 22 is a light emitting diode (LED).

The fog generator 30 is received in the censer body 10 to convert the working fluid 13 to fog. The fog is guided into the chamber 241 by a guiding tube 31 and exhausted from the chamber 241 from the top end of the chamber 241. One end of the guiding tube 31 is inserted in the fog generator 30, and the other end of the guiding tube 31 is received in the chamber 241. In this embodiment, a bottom end of the fog generator 30 is located in the working fluid 13, and the fog generator 30 includes an electric heating wire to heat the working fluid 13 to generate fog.

The controller 40 is mounted on an inner surface of the top cover 11. The sensor 50 is mounted on an outer side of the bottom cover 12. The controller 40 connects the fog generator 30 and the sensor 50.

When the light source 22 is lighted, the sensor 50 senses a distance between the sensor 50 and a person located at a periphery of the sensor 50 and a corresponding diction signal occurs in the sensor 50. The diction signal is transferred to the controller 40, and then the controller 40 adjusts the fog generator 30 on or off. When the distance is large enough, the controller 40 adjusts the fog generator 30 off. When the distance is located at a determined range, the controller 40 adjusts the fog generator 30 on.

It is to be further understood that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. An electronic censer, comprising:
   an incense branch comprising a light guiding tube, a light source and a head member mounted on opposite ends of the light guiding tube, and a fog guiding tube surrounding the light guiding tube, the fog guiding tube spaced from the light guiding tube to define a chamber therebetween, and light emitted from the light source guided by the light guiding tube and traveling through the head member to illuminate; and
   a fog generator generating fog, and the fog being guided to the chamber to be exhausted.

2. The electronic censer of claim 1 further comprising a censer body, wherein the censer body is a hollow container and comprises a bottom cover and a top cover engaging with the bottom cover, and a bottom end of the incense branch extends through the top cover and is mounted on the top cover.

3. The electronic censer of claim 2, wherein working fluid is contained in the censer body, the fog generator is received in the censer body and part of the fog generator is located in the working fluid to convert the working fluid into the fog.

4. The electronic censer of claim 2, wherein the light guiding tube is a transparent tube, a bottom portion of the light guiding tube extends through the top cover and is mounted on the top cover, a top portion of the light guiding tube is beyond the top cover, the light source is received in the bottom portion and located in the censer body, and the head member is mounted on a top end of the top portion.

5. The electronic censer of claim 4, wherein a bottom end of the fog guiding tube is mounted on the top cover to make a bottom end of the chamber be closed by the top cover.

6. The electronic censer of claim 1 further comprising a sensor and a controller connecting the fog generator and the sensor.

7. The electronic censer of claim 1, wherein the light source is a light emitting diode.

8. The electronic censer of claim 1, wherein the head member is made of glass or plastic.

9. An electronic censer, comprising:
a censer body;
working fluid contained in the censer body;
an incense branch comprising a light guiding tube, a light source mounted on the light guiding tube, and a fog guiding tube surrounding the light guiding tube and spaced from the light guiding tube to define a chamber between the fog guiding tube and the light guiding tube;
a fog generator received in the censer body and for converting the working fluid to fog; and
a guiding tube guiding the fog from the censer body to the chamber to exhaust.

10. The electronic censer of claim 9, wherein a bottom end of the fog guiding tube is mounted on the censer body to make a bottom end of the chamber be closed by the censer body.

11. The electronic censer of claim 9, wherein a bottom end of the fog generator is located in the working fluid, and the fog generator comprises an electric heating wire to heat the working fluid.

12. The electronic censer of claim 9, wherein the light guiding tube is a cylindrical, transparent tube.

13. The electronic censer of claim 9, wherein the fog guiding tube is opaque.

14. The electronic censer of claim 9, wherein a head member is mounted on a top end of the light guiding tube and covers the top end of the light guiding tube.

15. The electronic censer of claim 14, wherein the head member is transparent and made of glass or plastic.

16. The electronic censer of claim 14, wherein a top end of the fog guiding tube is coplanar with a bottom end of the head member.

17. The electronic censer of claim 9, wherein a sensor is mounted on an outside of the censer body.

18. The electronic censer of claim 17, wherein a controller is received in the censer body and electrically connects the sensor and the fog generator.

* * * * *